United States Patent [19]

Stokker

[11] Patent Number: 4,902,709

[45] Date of Patent: Feb. 20, 1990

[54] NOVEL ANTIHYPERCHOLESTEROLEMIC COMPOUNDS

[75] Inventor: Gerald E. Stokker, Gwynedd Valley, Pa.

[73] Assignee: Merck & Co., Inc., Rahway, N.J.

[21] Appl. No.: 231,322

[22] Filed: Aug. 12, 1988

Related U.S. Application Data

[62] Division of Ser. No. 26,512, Mar. 17, 1987, Pat. No. 4,789,682.

[51] Int. Cl.$^4$ ............................................. A61K 31/19
[52] U.S. Cl. ...................... 514/428; 514/438; 514/532; 514/539; 514/558; 514/559; 514/569; 514/630; 514/824; 548/557; 548/566; 549/74; 549/79; 560/56; 560/60; 560/45; 560/17; 562/470; 562/426; 562/452
[58] Field of Search ...................... 562/470, 426, 452; 560/56, 17, 45, 60; 564/218, 219, 217, 305; 514/559, 630, 532, 539, 558, 569, 438, 428; 548/557, 566; 549/74, 79

[56] References Cited

U.S. PATENT DOCUMENTS 4,710,513  12/1987  Willard et al. ...................... 514/460

Primary Examiner—Glennon H. Hollrah
Assistant Examiner—Amelia A. Owens
Attorney, Agent, or Firm—Melvin Winokur; Joseph F. DiPrima

[57] ABSTRACT

Novel antihypercholesterolemic compounds of structure (I) or (II),

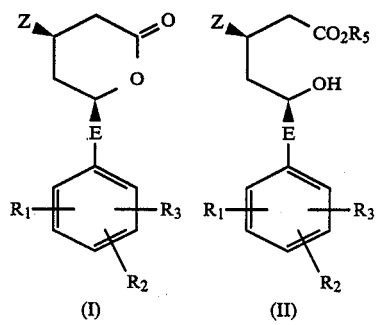

pharmaceutically acceptable salts, thereof and a novel process for preparing compounds of structure I, are disclosed.

8 Claims, No Drawings

NOVEL ANTIHYPERCHOLESTEROLEMIC COMPOUNDS

This is a division of application Ser. No. 026,512, filed Mar. 17, 1987 now U.S. Pat. No. 4,789,682.

BACKGROUND OF THE INVENTION

Hypercholesterolemia is known to be one of the prime risk factors for ischemic cardiovascular disease, such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semisynthetic and totally synthetic analogs thereof.

The naturally occurring compounds and their semisynthetic analogs have the following general structural formulae:

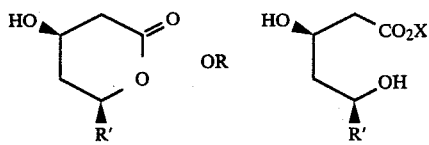

wherein
X is hydrogen, $C_{1-5}$alkyl or $C_{1-5}$alkyl substituted with a member of the group consisting of phenyl, dimethylamino or acetylamino;
R' is

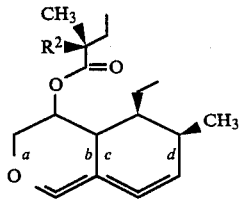

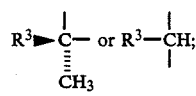

$R^3$ is hydrogen or hydroxy;
$R^2$ is hydrogen or methyl; and
a, b, c and d are single bonds, one of a, b, c and d is a double bond or a and c or b and d are double bonds provided that when a is a double bond, Q is

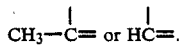

The totally synthetic antihypercholesterolemic compounds are disclosed in U.S. Pat. No. 4,375,475 and have the following general structural formulae:

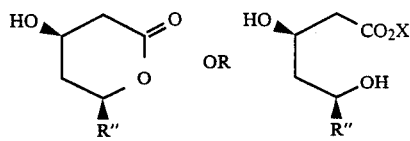

wherein R" is:

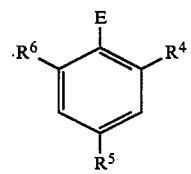

wherein:
E is $-CH_2-$, $-CH_2CH_2-$ or $-CH=CH-$;
$R^4$ and $R^5$ are independently $C_{1-3}$alkyl, fluoro, bromo or chloro; and
$R^6$ is phenyl, benzyloxy, substituted phenyl or substituted benzyloxy in which the phenyl group in each case is substituted with one or more substituents selected from $C_{1-3}$alkyl, fluoro, bromo or chloro.

Copending patent application Ser. No. 912,867 filed Sept. 29, 1986 discloses diaminoacyl derivatives of compactin, mevinolin and the totally synthetic HMG-CoA reductase inhibitors of structural formula:

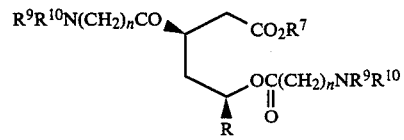

wherein R, $R^7$, $R^{98}$ and $R^{10}$ and n are defined in the above cited application.

In relationship to the process of the instant invention, Cacchi and co-workers have carried out Michael type additions of aryl iodides to acyclic α, β-unsaturated aldehydes and ketones in the presence of a catalytic amount of Pd[II]and an excess of trialkylammonium formate. (3. Cacchi, F. LaTorre, G. Palmier; *J. Organometallic Chem.*, 1984, 268, C48; S. Cacchi, G. Palmieri, Synthesis, 1984, 575.)

SUMMARY OF THE INVENTION

This invention relates to novel compounds which are HMG-CoA reductase inhibitors and a novel process for Preparing said compounds. The compounds of the instant invention have the structure (I) or (II):

in which Z is an aryl, heteroaryl or substituted aryl or heteroaryl group. These compounds are formed in a sequence of reactions in which a hydroxy group at the 4-position of the lactone moiety is replaced by the group Z.

DETAILED DESCRIPTION OF THE INVENTION

This invention relates to new antihypercholesterolemic compounds having the structure (I) or (II) and a novel process for preparing said compounds:

wherein

Z is phenyl, naphthyl, thiophenyl, thiazyl, pyrryl; or phenyl, naphthyl, thiophenyl, thiazyl, pyrryl substituted with a group A, A is $C_{1-5}$alkyl, Cl, F, OH, $C_{1-5}$alkyloxy, $C_{2-6}$alkanoylamiro, $C_{1-5}$alkyloxycarbonyl, phenyl, hydroxyalkyl, trifluromethyl-$C_{2-8}$alkanoylamino;

E is a direct bond, —$CH_2$—, —$CH_2CH_2$—;

$R_1$, $R_2$ and $R_3$ are each selected from H, Cl or F, $C_{1-4}$ alkyl, $C_{1-4}$ chloroalkyl, $C_{1-4}$ fluroalkyl, phenyl, phenyl substituted by chlorine or fluorine, $C_{1-4}$ alkyoxy $C_{2-8}$ alkanoyloxy, $C_{2-8}$ alkanoyloxy-$C_{1-5}$ alkyl, and $OR_4$ in which $R_4$ is H, $C_{2-8}$ alkanoyl, benzoyl, phenyl, chlorophenyl or flurophenyl, phenyl $C_{1-3}$ alkyl, $C_{1-8}$ alkyl, $C_{1-4}$ chloroalkyl or $C_{1-4}$ flurcalkyl cycloalkyl-$C_{1-3}$ alkyl, adamantyl-$C_{1-3}$ alkyl, or substituted Phenyl-$C_{1-3}$ alkyl, in which the substituents are selected from: chlorine or fluorine, $C_{1-4}$ alkyoxy, $C_{1-4}$ alkyl, or $C_{1-4}$ chloroalkyl, $C_{1-4}$ fluroalkyl;

$R^5$ is hydrogen, $C_{1-5}$alkyl or $C_{1-5}$alkyl substituted with a member of the group consisting of phenyl, dimethylamino, or acetylamino; and Pharmaceutically acceptable salts of the compounds (II) in which $R_5$ is hydrogen.

A preferred embodiment of this invention relates to those structures of general formula I and II wherein Z is phenyl or thiophenyl; or phenyl substituted with: phenyl, $C_{1-5}$alkyloxy, hydroxy, hydroxyalkyl, $C_{1-5}$ alkyloxycarbonyl, C2-8- alkanoyloxy, or trifluromethyl-$C_{2-8}$alkanoylamino;

E is —$CH_2CH_2$—;

$R_1$, $R_2$ and $R_3$ are each selected from H, Cl or F, and the corresponding dihydroxy acids resulting from the hydrolytic opening of the lactone ring and the pharmaceutically acceptable salts of the dihydroxy acids, and the $C_{1-3}$alkyl and phenyl, dimethylamino or acetylamino-substituted-$C_{1-3}$ alkyl esters of the dihydroxy acids.

A more preferred embodiment of the present invention comprises those structures of general formula I wherein Z is phenyl: or phenyl substituted with: phenyl, $C_{1-5}$alkyloxy, hydroxy, hydroxy-$C_{1-5}$alkyl, $C_{1-5}$alkyloxycarbonyl, or trifluromethyl-$C_{2-8}$alkanoylamino;

E is —$CH_2CH_2$—;

$R_1$ is hydrogen, $R_2$ and $R_3$ are each chloro in the 2 and 4 positions.

The compounds of this invention are useful as antihypercholesterolemic agents for the treatment of arteriosclerosis, hyperlipidemia, familial hypercholesterolemia and the like diseases in humans. They may be administered orally or parentally in the form of a capsule, a tablet, an injectable preparation or the like. It is usually desirable to use the oral route. Doses may be varied, depending on the age, severity, body weight and other conditions of human patients but daily dosage for adults is within a range of from about 10 mg to 2 g (preferably 10 to 500 mg) which may be given in two to four divided doses, higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly [methyl-(3-tri-methyl aminopropyl-)imino-trimethylene dihalide]. The relative amounts of the compounds of this invention and these polymers is between 1:1 and 1:15,000.

The intrinsic HMG-CoA reductase inhibition of the claimed compounds is measured following the in vitro procedure detailed in U.S. Pat. No. 4,668,699.

Representative of the intrinsic HMG-CoA-reductase inhibition of the claimed compounds are the $IC_{50}$ values for the 2,4 dichloro derivatives of formula I.

| wherein Z = | phenyl | $IC_{50}$ = | 21.0 μM |
|---|---|---|---|
| | 4-$C_6H_5C_6H_4$ | | 33.6 μM |
| | 4-$CH_3O$—$C_6H_4$ | | 43.5 μM |
| | 4-HO—$C_6H_4$ | | 20.8 μM |
| | 2-HO—$CH_2C_6H_4$ | | 42.0 μM |

Included within the scope of this invention is the method of treating arteriosclerois, familial hypercholesterolemia or hyperlipidemia which comprises administering to a subject in need of such treatment a nontoxic therapeutically effective amount of the compounds of formula (I) or (II) or pharmaceutical compositions thereof.

Another embodiment of the instant invention is a process for the preparation of a compound of structure (I) by the palladium [0] catalyzed stereospecific addition of an aryl or heteroaryl iodide to a compound of structure (IV) in the presence of a trialkylamine.

The compounds of the instant invention represented by structural formula (I) are prepared according to the scheme in Flow Sheet I.

Flow Sheet I
General Scheme for Preparation of Compounds of Structure (I)

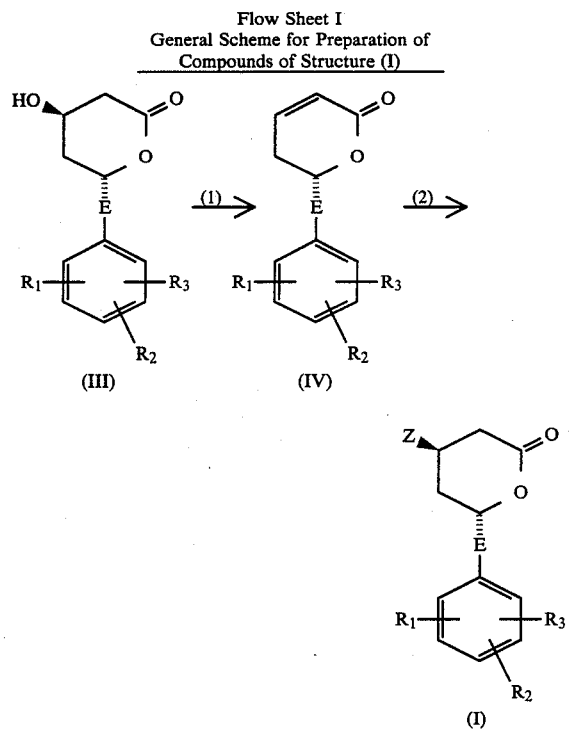

Starting compounds of structure III) are prepared according to the Procedures disclosed in U.S. Pat. No. 4,375,475. In step (1) of flow sheet I the 4-hydroxy group in the lactone moiety is acetylated and the elements of acetic acid eliminated to yield the $\alpha, \beta$ unsaturated lactone (IV). The reaction is conducted by slowly adding acetyl chloride to a mixture of (III), chloroform, triethylamine and 4,4-dimethylaminopyridine at ambient temperatures.

Step (2) is a novel process in which the formed double bond in the lactone moiety is arylated stereospecifically using an aromatic iodide and Pd(0) as a catalyst with a trialkylamine. The trialkylamine must have at least one hydrogen in the $\alpha$ or $\beta$ position. Possible amines include triethylamine, tribenzylamine and triisopropylamine. The preferred amine is triethylamine. The Pd[0] catalyst can be selected from tetrakis(triphenylphosphine)palladium, palladium on carbon, or Pd[0] generated in situ. The preferred palladium catalyst is tetrakis(triphenylphosphine)palladium. The aromatic iodide is commercially available or prepared according to standard chemical transformations. The palladium catalyst is commercially available.

The product (I) lactone can be converted into the corresponding dihydroxy acid and a pharmaceutically acceptable salt of said acid and the $C_{1-3}$alkyl, phenyl, dimethylamino or the acetylamino-substituted-$C_{1-3}$alkyl esters of the dihydroxy acids using procedures disclosed in U.S. Pat. No. 4,375,475.

The following examples illustrate the present invention and as such are not to be considered as limiting the invention set forth in the claims appended hereto.

EXAMPLE I

Preparation of trans-6-[2-(2,4-dichlorophenyl)ethyl]-3,4,5,6-tetrahydro-4-phenyl-2H-pyran-2-one (a) 6-[2-(2,4 dichlorophenyl)ethyl]-5,6-dihydro-2H-pyran-2-one (1a)

Acetyl chloride (8.6 ml) was added slowly to a vigorously stirred solution of trans-6-[2-(2,4-dichlorophenyl)ethyl]-3,4,5,6-tetrahydro-4-hydroxy-2H-pyran-2-one (19.3 g, 66.8 mmol), CHCl₃ (200 ml), triethylamine (35 ml) and 4-(dimethylasmino)pyridine (100 mg) at 20° C. The cloudy Pale amber mixture was stirred at ambient temperature for 16 hours and then distributed between diethyl ether (300 ml) and H₂O (300 ml). The organic layer was separated and washed with 1N HCl 200 ml) and H₂O (2×200 ml), then dried and evaporated. The pale amber residual oil slowly solidified. Crystallization from n-butyl chloride:hexane; 1:5(v:V) provided the title compound as small pale amber needles. m.p. 69°–70° C.

Anal for $C_{13}H_{12}O_2Cl_2$ Calc'd C: 57.59 H: 4.46. Found C: 57.56 H: 4.50.

H¹NMR (300 MHz, CDCl₃) δ 1.90–2.12 (m, 2H, ArCH₂CH₂—), 2.35–2.40 (m, 2H,—CH₂CH=CH—), 2.85 (ddd, H, ArCHCH₂, J=6, 8, 17Hz), 3.0 (ddd, H, ArCHCH₂, J=5, 8, 17 Hz), 4.37–4.46 (m, H, —CHOCO), 6.04 (dt, H, —C=CHCO, J=9.6, 1.8 Hz), 6.88 (ddd, H, —CH₂CH=C—, J=4.1, 4.6, 9.6 Hz), 7.16–7.22 (m, 2H, ArH), 7.36 (d, H, ArH, J=1Hz).

(b) trans-6-[2-(2,4-dichlorophenyl)ethyl]-3,4,5,6-tetrahydro-4-phenyl-2H-pyran-2-one A mixture of compound (1a) 270 mg, 1.0 mmol), iodobenzene (224 mg, 1.1 mmol), triethylamine (160 μl, 1 1 mmol) and tetrakis(triphenylphosphine)palladium (10 mg) was placed under argon and heated at 80° C. for 16 hours. The dark mixture was cooled and distributed between ethyl acetate 100 ml) and 1N HCl (100 ml). The organic layer was separated and washed with water (2×50 ml), dried and evaporated. The residue was purified by flash chromatography on silica gel using CHCl₃:acetone, 20:1 (V:V) as eluant.

Anal for $C_{19}H_{18}O_2Cl_2$. 0.1CHCl₃ Calc'd C: 63.51 H: 5.05. Found C: 63.48 H: 5.14.

H¹ NMR (300 MHz, CDCl₃), δ 1.84–2.0 (m, 2H, ArCH₂CH₂—) 2.0–2.18 (m, 2H, —CH₂CHOCO), 2.72–2.89 (m, 3H, ArCHCH₂ and —CH₂CO—), 2.98 (ddd, H, ArCHCH₂—, J̄=5,8,17Hz) , 3.39 (dddd, H, ArCH, H, J=6̄,6,6, 8 Hz) , 4.42 (dddd, H, —CHOCO, J=5,5,8,8Hz) , 7.18–7.4 (m, 8H, ArH).

EXAMPLES 2–10

By substituting an equimolar amount of the following iodoaryl compound for iodobenzene in Step (b) of example 1 and otherwise following the procedure of Example 1, there was obtained the following compounds of the instant invention.

| Aryl Iodide | $Z^a$ | $H^b$ at C-4 (dddd) |
|---|---|---|
| 2 4-C₆H₅—C₆H₄I | 4-C₆H₅C₆H₄ | 3.42 |

-continued

| Aryl Iodide | $Z^a$ | $H^b$ at C-4 (dddd) |
|---|---|---|
| 3  4-CH$_3$O$_2$C—C$_6$H$_4$I | 4-CH$_3$O$_2$CC$_6$H$_4$— | 3.46 |
| 4  4-CH$_3$O—C$_6$H$_4$I | 4-CH$_3$OC$_6$H$_4$— | 3.33 |
| 5  4-HO—C$_6$H$_4$I | 4-HOC$_6$H$_4$— | 3.30 |
| 6  4-F$_3$CCO$_2$NH—C$_6$H$_4$I | 4-F$_3$CCO$_2$NHC$_6$H$_4$— | 3.36 |
| 7  3-CH$_3$OC$_6$H$_4$I | 3-CH$_3$OC$_6$H$_4$— | 3.36 |
| 8  2-HOCH$_2$C$_6$H$_4$I | 2-HOCH$_2$C$_6$H$_4$— | 3.75 |
| 9  2-CH$_3$OC$_6$H$_4$I | 2-CH$_3$OC$_6$H$_4$— | 3.58 |
| 10  3-iodothiophene | 3-thiophenyl | 3.47 |

$^a$Isolated pure compounds as oils, each gave satisfactory, NMR data and elementary combustion analysis.
$^b$Diagnostic signal for the C-4 methine of the trans arylated product. Spectra obtained on a Varian XL-300 spectrometer in CDCl$_3$. Chemical shifts given in δ values relative to TMS.

EXAMPLE 11

Preparation of Ammonium Salt of Compound II

The lactone from Example 1 (347 mg, 1 mmol) is dissolved with stirring in 0.1 N NaOH (1.1 mmol) at r.t. The resulting solution is cooled to 0° C. and acidified by the dropwise addition of 1N HCl. The resulting mixture is extracted with ether (2×50 ml) and the ether extracts are combined, washed with brine (3×25 ml) and dried (MgSO$_4$). The MgSO$_4$ is removed by filtration and the filtrate saturated with ammonia (gas) to give a gum which solidifies to provide the ammonium salt. The solid can be recrystallized by dissolution in warn (CH$_3$CN/conc. NH$_4$OH (4:1; v:v, 4 ml) followed by dilution with CH$_3$CN.

EXAMPLE 12

Preparation of Alkali and Alkaline Earth Salts of Compound II

To a solution of 35 mg of the lactone from Example 1 in 2 ml of ethanol is added 1 ml of aqueous NaOH (1 equivalent). After one hour at room temperature, the mixture is taken to dryness in vacuo to yield the sodium salt of Compound II.

In like manner the potassium salt is prepared using one equivalent of potassium hydroxide, and the calcium salt using one equivalent of CaO.

EXAMPLE 13

Preparation of Ethylenediamine Salt of Compound II

To a solution of 0.40g of the ammonium salt of Compound II from Example 11 in 10 ml of methanol is added 75 μl of ethylenedimine. The methanol is stripped off under vacuum to obtain the ethylenediamine salt of Compound II.

EXAMPLE 14

Preparation of Tris(hydroxymethyl)aminomethane Salt of Compound II

To a solution of 170 mg of the ammonium salt of Compound II from Example 11 in 5 ml of methanol is added a solution of 60.5 mg of tris(hydroxymethyl) aminomethane in 5 ml of methanol. The solvent is removed in vacuo to afford the desired tris(hydroxymethyl)aminomethane salt of Compound II

EXAMPLE 15

Preparation of L-Lysine Salt of Compound II

A solution of 0.001 mole of L-lysine and 0.0011 mole of the ammonium salt of Compound II from Example 11 in 15 ml of 85% ethanol is concentrated to dryness in vacuo to give the L-lysine salt of Compound II.

Similarly prepared are the L-arginine, L-ornithine, and N-methylglucamine salts of Compound II.

EXAMPLE 16

Preparation of Tetramethylammonium Salt of Compound II

A mixture of 60 mg of Compound II from Example 11 in 2 ml of methylene chloride and 0.08 ml of 24% tetramethylammonium hydroxide in methanol is diluted with ether to Yield the tetramethylammonium salt of compound II.

EXAMPLE 17

Preparation of Methyl Ester of Compound II

To a solution of 335 mg of the lactone from Example 1 in 100 ml of absolute methanol is added 10 ml 0.1 M sodium methoxide in absolute methanol. This solution is allowed to stand at room temperature for one hour, is then diluted with water and extracted twice with ethyl acetate; the ethyl acetate, dried over anhydrous sodium sulfate, is removed in vacuo to Yield the methyl ester of Compound II.

In like manner, by the use of equivalent amounts of propanol, butanol, isobutanol, t-butanol, amylalcohol, isoamylalcohol, 2-dimethyl, aminoethanol, benzylalcohol, phenethanol, 2-acetamidoethanol, and the like, the corresponding esters are obtained.

EXAMPLE 18

Preparation of free Hydroxy Acids

The sodium salt of the compound II from Example 12 is dissolved in 2 ml of ethanol-water (1:1) and added to 10 ml of 1N hydrochloric acid from which the hydroxy acid is extracted with ethyl acetate. The latter solvent is washed once with water, dried, and removed in vacuo with a bath temperature not exceeding 30° C. The hydroxy acid derived slowly reverts to the lactone on standing.

EXAMPLE 19

As a specific embodiment of a composition of this invention, 20 mg of the lactone from Example 1 is formulated with sufficient finely divided lactose to provide a total amount of 580 to 590 mg to fill a size 0 hard gelatin capsule.

What is claimed is:

1. A compound of structural formula (II):

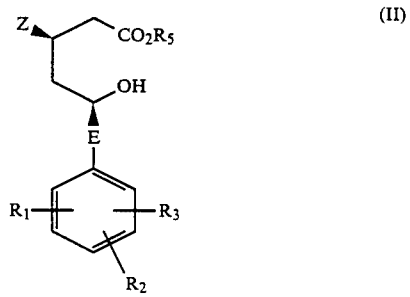

(II)

wherein
  Z is phenyl, naphthyl, thiophenyl, pyrryl; or phenyl, naphthyl, thiophenyl, pyrryl substituted with a group A;

A is selected from a group consisting of: Cl, F, OH, $C_{1-5}$alkyl, $C_{1-5}$alkyloxy, $C_{2-8}$alkanoyloxy, $C_{2-6}$alkanoylamino, $C_{1-5}$alkyloxycarbonyl, phenyl, hydroxy-$C_{1-5}$alkyl, trifluromethyl-$C_{2-8}$alkanoylamino;

E is a direct bond, —$CH_2$—, —$CH_2CH_2$— $R_1$, $R_2$, $R_3$ are each selected from: H, Cl, or F, $C_{1-4}$alkyl, $C_{1-4}$chloroalkyl or $C_{1-4}$fluroalkyl, phenyl, phenyl substituted by Cl or F, $C_{1-4}$alkyloxy. $C_{2-8}$alkanoyloxy $C_{2-8}$-Balkanoyloxy-$C_{1-5}$ alkyl, and $OR_4$ in which $R_4$ is H, $C_{2-8}$alkanoyl, benzoyl phenyl, chlorophenyl or flurophenyl, phenyl-$C_{1-3}$alkyl, $C_{1-8}$alkyl, $C_{1-4}$chloroalkyl or $C_{1-4}$fluroalkyl, cycloalkyl-$C_{1-3}$alkyl, adamantyl-$C_{1-3}$alkyl, or substituted Phenyl-$C_{1-3}$alkyl in which the substituents are selected from: chlorine or fluorine, $C_{1-4}$alkyloxy, $C_{1-4}$alkyl, $C_{1-4}$chloroalkyl or $C_{1-4}$fluroalkyl;

$R_5$ is hydrogen, $C_{1-5}$ alkyl or $C_{1-5}$ alkyl substituted with a member of the group consisting of phenyl, dimethylamino, or acetylamino; and a pharmaceutically acceptable salt of the compound (II) in which $R_5$ is hydrogen.

2. A compound of claim 1 wherein:
Z is phenyl or thiophenyl; or phenyl substituted with a group A; and
E is —$CH_2CH_2$—.

3. A compound of claim 2 wherein:

A is selected from a group consisting of: OH, $C_{1-5}$alkyloxy, $C_{1-5}$alkyloxycarbonyl, phenyl, trifluromethyl-$C_{2-8}$alkanoylamino, hydroxy $C_{1-5}$alkyl.

4. A compound of claim 3 wherein:
$R_1$, $R_2$ and $R_3$ are each selected from: H, Cl or F.

5. A compound of claim 4 wherein:
$R_1$ is hydrogen, $R_2$ and $R_3$ are each chloro in the 2 and 4 positions.

6. A compound of claim 5 selected from the group wherein $R_5$ is H and
  a. Z is phenyl,
  b. Z is 4—$C_6H_5$—$C_6H_4$—,
  c. Z is 4—$CH_3O$-$C_6H_4$—,
  d. Z is 4—HO—$C_6H_4$—,
  e. Z is 2—HO—$CH_2C_6H_4$—,
  f. Z is 4—$CH_3O_2C$—$C_6H_4$—,
  g. Z is 4—$F_3CCO_2NH$—$C_6H_4$—,
  h. Z is 3—$CH_3O$—$C_6H_4$—,
  i. Z is 3—thiophenyl.

7. A hypocholesterolemic, hypolipidemic pharmaceutical composition comprising a nontoxic therapeutically effective amount of a compound of claim 1 and a pharmaceutically acceptable carrier.

8. A method of inhibiting cholesterol biosynthesis comprising the administration to a subject in need of such treatment a nontoxic therapeutically effective amount of a compound of claim 1.

* * * * *

UNITED STATES PATENT AND TRADEMARK OFFICE
CERTIFICATE OF CORRECTION

PATENT NO. : 4,902,709

DATED : February 20, 1990

INVENTOR(S) : Stokker

It is certified that error appears in the above-identified patent and that said Letters Patent is hereby corrected as shown below:

In the abstract, delete

" 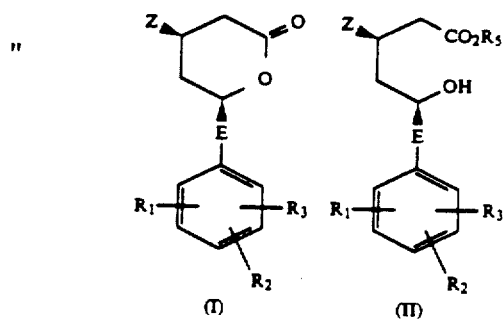 "

and insert therefor

-- 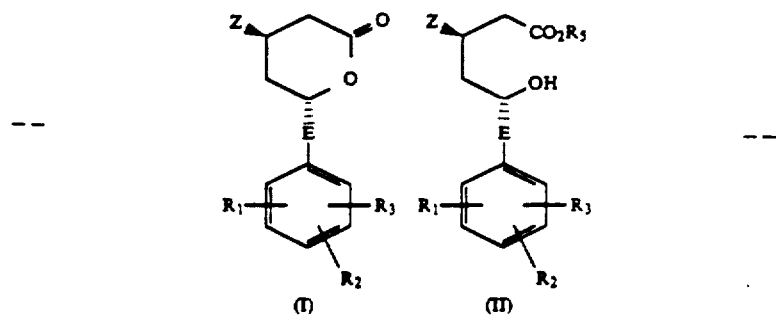 --

UNITED STATES PATENT AND TRADEMARK OFFICE
CERTIFICATE OF CORRECTION

PATENT NO. : 4,902,709

DATED : February 20, 1990

INVENTOR(S) : Stokker

It is certified that error appears in the above-identified patent and that said Letters Patent is hereby corrected as shown below:

At column 3, line 30, delete

" 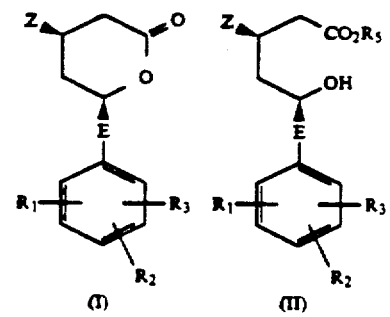 "

and insert therefor

-- 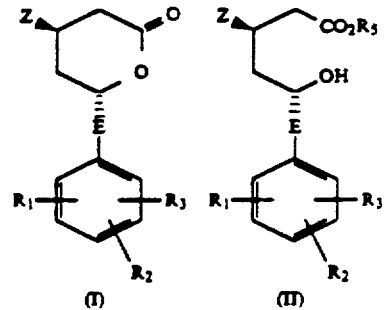 --

UNITED STATES PATENT AND TRADEMARK OFFICE
CERTIFICATE OF CORRECTION

PATENT NO. : 4,902,709

DATED : February 20, 1990

INVENTOR(S) : Stokker

It is certified that error appears in the above-identified patent and that said Letters Patent is hereby corrected as shown below:

At column 8, line 55, delete

" 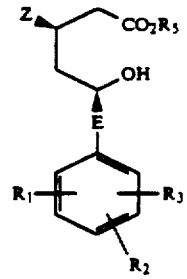 "

and insert therefor -- 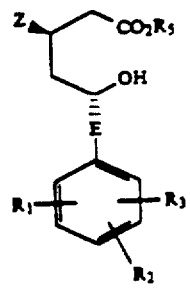 --

Signed and Sealed this

Third Day of September, 1991

*Attest:*

HARRY F. MANBECK, JR.

*Attesting Officer*   Commissioner of Patents and Trademarks